US006770061B2

(12) United States Patent
Wildman

(10) Patent No.: US 6,770,061 B2
(45) Date of Patent: Aug. 3, 2004

(54) LOW EXPOSURE WASTE DISPOSAL SUCTION SYSTEM AND ASSOCIATED METHOD

(75) Inventor: Timothy D. Wildman, Metamora, IN (US)

(73) Assignee: Hill-Rom Services, Inc., Batesville, IN (US)

(*) Notice: Subject to any disclaimer, the term of this patent is extended or adjusted under 35 U.S.C. 154(b) by 178 days.

(21) Appl. No.: 10/022,310

(22) Filed: Dec. 14, 2001

(65) Prior Publication Data

US 2002/0082569 A1 Jun. 27, 2002

Related U.S. Application Data

(60) Provisional application No. 60/256,590, filed on Dec. 19, 2000.

(51) Int. Cl.$^7$ ................................. A61M 1/00
(52) U.S. Cl. ........................ 604/319; 604/540
(58) Field of Search ........................... 604/326, 289, 604/290, 313, 315, 317, 318, 319, 322, 540

(56) References Cited

U.S. PATENT DOCUMENTS

| | | | |
|---|---|---|---|
| 1,973,990 A | * | 9/1934 | Marrinan .................... 604/317 |
| 2,195,771 A | | 4/1940 | Estler |
| 3,520,300 A | | 7/1970 | Flower, Jr. |
| 3,935,863 A | | 2/1976 | Kliger |
| 4,135,515 A | | 1/1979 | Muriot |
| 4,396,386 A | | 8/1983 | Kurtz et al. |
| 4,444,548 A | | 4/1984 | Andersen et al. |
| 4,455,140 A | | 6/1984 | Joslin |
| 4,457,755 A | | 7/1984 | Wilson |
| 4,465,485 A | | 8/1984 | Kashmer et al. |
| 4,525,166 A | | 6/1985 | Leclerc |
| 4,533,352 A | | 8/1985 | Beek et al. |

(List continued on next page.)

FOREIGN PATENT DOCUMENTS

| | | |
|---|---|---|
| EP | 0651977 A1 | 5/1995 |
| EP | 0853950 A1 | 7/1998 |
| GB | 2220357 A | 1/1990 |
| WO | WO00/07653 | 2/2000 |
| WO | WO01/37922 | 5/2001 |

OTHER PUBLICATIONS

*RED>AWAY—Infectious Fluid Collection and Disposal System*, Dornoch Medical Systems, Inc., two pages, date unknown.

*OSCAT System—On Site Containment and Treatment Suction Fluid Management System*, MediVators, Inc., six pages, 1999.

*VAC–U–PORT Confined Liquid Infectious Waste Management System*, Bemis Manufacturing Company , twelve pages, 1996.

Primary Examiner—John J. Calvert
Assistant Examiner—Michael G Bogart
(74) Attorney, Agent, or Firm—Barnes & Thornburg

(57) ABSTRACT

An apparatus for collecting and disposing of fluid waste from a patient undergoing a medical procedure in an operating room comprises a tank and a conduit. The tank is positioned outside the operating room. The conduit extends from the tank and into the operating room. Fluid waste from the patient is suctioned through the conduit and collected in the tank. A method for collecting and disposing of fluid waste from a patient undergoing a medical procedure is also disclosed.

38 Claims, 2 Drawing Sheets

U.S. PATENT DOCUMENTS

| | | | |
|---|---|---|---|
| 4,553,966 A | 11/1985 | Korteweg | |
| 4,578,060 A | 3/1986 | Huck et al. | |
| 4,642,093 A | 2/1987 | Harle | |
| 4,648,870 A | 3/1987 | Goldberg et al. | |
| 4,661,093 A | 4/1987 | Beck et al. | |
| 4,681,562 A | 7/1987 | Beck et al. | |
| 4,713,052 A | 12/1987 | Beck et al. | |
| 4,735,606 A | 4/1988 | Davison | |
| 4,747,166 A | 5/1988 | Kuntz | |
| 4,798,583 A | 1/1989 | Beck et al. | |
| 4,820,284 A | 4/1989 | Hauri | |
| 4,830,047 A | 5/1989 | Hodge | |
| 4,921,492 A | 5/1990 | Schultz et al. | |
| 4,930,997 A | 6/1990 | Bennett | |
| 5,002,528 A | 3/1991 | Palestrant | |
| 5,014,389 A | 5/1991 | Ogilvie et al. | |
| 5,019,059 A | 5/1991 | Goldberg et al. | |
| 5,034,006 A | 7/1991 | Hosoda et al. | |
| 5,045,077 A | 9/1991 | Blake | |
| 5,073,172 A | 12/1991 | Fell | |
| 5,102,404 A | 4/1992 | Goldberg et al. | |
| 5,176,667 A | 1/1993 | DeBring | |
| 5,215,539 A | 6/1993 | Schoolman | |
| 5,242,434 A * | 9/1993 | Terry | 604/317 |
| 5,254,080 A | 10/1993 | Lindsay | |
| 5,254,110 A * | 10/1993 | Marcus et al. | 604/322 |
| 5,264,026 A * | 11/1993 | Paul | 95/268 |
| 5,349,965 A | 9/1994 | McCarver | |
| 5,374,257 A | 12/1994 | Drainville et al. | |
| 5,409,511 A | 4/1995 | Paul | |
| 5,437,651 A | 8/1995 | Todd et al. | |
| 5,458,586 A | 10/1995 | Adiletta | |
| 5,466,229 A | 11/1995 | Elson et al. | |
| 5,468,234 A * | 11/1995 | Griffin et al. | 604/290 |
| 5,484,427 A | 1/1996 | Gibbons | |
| 5,484,428 A | 1/1996 | Drainville et al. | |
| 5,507,734 A | 4/1996 | Everett, Jr. et al. | |
| 5,618,410 A | 4/1997 | Wallace et al. | |
| 5,620,428 A | 4/1997 | Hand | |
| 5,624,418 A | 4/1997 | Shepard | |
| 5,628,735 A | 5/1997 | Skow | |
| 5,656,027 A | 8/1997 | Ellingboe | |
| 5,678,564 A | 10/1997 | Lawrence et al. | |
| 5,683,371 A | 11/1997 | Hand | |
| 5,688,255 A | 11/1997 | Hand | |
| 5,697,920 A | 12/1997 | Gibbons | |
| 5,741,237 A | 4/1998 | Walker | |
| 5,741,238 A | 4/1998 | Bradbury et al. | |
| 5,776,118 A | 7/1998 | Seifert et al. | |
| 5,776,260 A | 7/1998 | Dunn et al. | |
| 5,807,358 A | 9/1998 | Herweck et al. | |
| 5,807,359 A | 9/1998 | Bemis et al. | |
| 5,827,246 A | 10/1998 | Bowen | |
| 5,871,476 A | 2/1999 | Hand | |
| 5,911,222 A | 6/1999 | Lawrence et al. | |
| 5,914,047 A | 6/1999 | Griffiths | |
| 5,931,822 A | 8/1999 | Bemis et al. | |
| 5,944,703 A | 8/1999 | Dixon et al. | |
| 5,971,956 A | 10/1999 | Epstein | |
| 6,039,724 A | 3/2000 | Seifert et al. | |
| 6,045,516 A | 4/2000 | Phelan | |
| 6,056,731 A | 5/2000 | Koetke et al. | |
| 6,142,982 A | 11/2000 | Hunt et al. | |
| 6,152,902 A | 11/2000 | Christian et al. | |
| 6,156,004 A | 12/2000 | Tremaine et al. | |
| 6,210,383 B1 | 4/2001 | Want et al. | |
| 6,244,311 B1 | 6/2001 | Hand et al. | |
| 6,261,276 B1 | 7/2001 | Reitsma | |
| 6,447,492 B1 * | 9/2002 | Frohn | 604/322 |
| 6,585,708 B1 * | 7/2003 | Maaskamp | 604/317 |
| 6,585,709 B2 * | 7/2003 | Maimets | 604/355 |
| 6,673,055 B2 * | 1/2004 | Bemis et al. | 604/319 |

* cited by examiner

LOW EXPOSURE WASTE DISPOSAL SUCTION SYSTEM AND ASSOCIATED METHOD

This application claims priority under 35 U.S.C. 119(e) to U.S. Provisional Application Serial No. 60/256,590, filed Dec. 19, 2000, which is expressly incorporated by reference herein.

BACKGROUND AND SUMMARY

The present disclosure relates to an apparatus for collecting and disposing of fluid waste from a patient undergoing a medical procedure in an operating room. The present disclosure also relates to a method for collecting and disposing of fluid waste from a patient undergoing surgery.

Systems used during surgical procedures for collecting and disposing of fluid waste from patients are known. Sometimes fluid waste samples are taken for analysis prior to disposal of the fluid waste. In many conventional fluid waste collection and disposal systems, blood and other fluids are suctioned from a surgical site on a patient and are collected in one or more plastic, disposable suction canisters. The small canisters are typically included as part of a larger free-standing portable unit located within the operating room. Thus, premium space in the operating room is sometimes occupied by fluid waste collection and disposal systems.

When the fluid collection canisters become filled during the course of a surgical procedure, they are replaced with empty canisters. After the surgical procedure is completed the canisters containing the fluid waste from the surgery are usually placed in a larger container and transported through the hospital to a central collection location where either they are stored until being transported off-site for ultimate disposal or they are incinerated, or otherwise disposed of, at the hospital.

Handling of fluid collection canisters by caregivers and other hospital personnel creates a risk that the handlers may come into contact with the biological fluid contained in the canister, especially if the container has a leak. In addition, canisters containing biological fluid may inadvertently be dropped or damaged during handling. Hospitals sometimes add a solidifying agent into the canisters to minimize the potential for spillage and leakage. However, there still exists a risk that handlers will come into contact with the fluid waste despite the addition of the solidifying agent. Thus, a reduction in the amount of handling of canisters containing fluid waste reduces the chances that caregivers or hospital personnel will come into contact with the biological fluid waste.

According to the present disclosure, an apparatus for collecting and disposing of fluid waste from a patient undergoing a medical procedure in an operating room is provided. The apparatus comprises a tank and a conduit. The tank is positioned outside the operating room. The conduit extends from a location inside the operating room to the tank positioned outside the operating room. Fluid waste from the patient is suctioned through the conduit and into the tank for collection.

In some embodiments, the conduit is routed from the tank through a space above a ceiling of the operating room and then downwardly through one or more arms suspended from the ceiling in the operating room. In other embodiments, the conduit is routed from the tank through a floor of the operating room and then upwardly into the operating room. In still other embodiments, the conduit is routed from the tank through a wall of the operating room.

In an illustrative embodiment, the apparatus has components for sampling the fluid collected in the tank, components for flushing or draining the contents of the tank into a sanitary sewage line, and components for cleaning the tank after the contents are flushed or drained. In addition, the tank of the illustrative embodiment has a transparent window that permits caregivers to view the contents of the tank. Graduated markings are associated with the window so that caregivers are able to determine accurately the volume of the fluid waste in the tank. The illustrative tank has a narrow, lower portion and a broad, upper portion so that the volume of smaller amounts of fluid collected in the lower portion are measured more accurately.

A method for collecting and disposing of fluid waste from a patient undergoing a medical procedure in an operating room is also disclosed. The method comprises the steps of creating a negative pressure in a tank positioned outside the operating room and suctioning fluid waste from the patient through a conduit that is routed from the tank into the operating room.

Additional features will become apparent to those skilled in the art upon consideration of the following detailed description of illustrative embodiments exemplifying the best mode of carrying out the disclosure as presently perceived.

BRIEF DESCRIPTION OF THE DRAWINGS

The detailed description particularly refers to the accompanying figures in which.

Corresponding reference characters indicate corresponding parts throughout the several views. The exemplification set out herein illustrates an embodiment in one form, and such exemplification is not to be construed as limiting the scope of the invention in any manner.

DETAILED DESCRIPTION OF THE DRAWINGS

Figure 1:
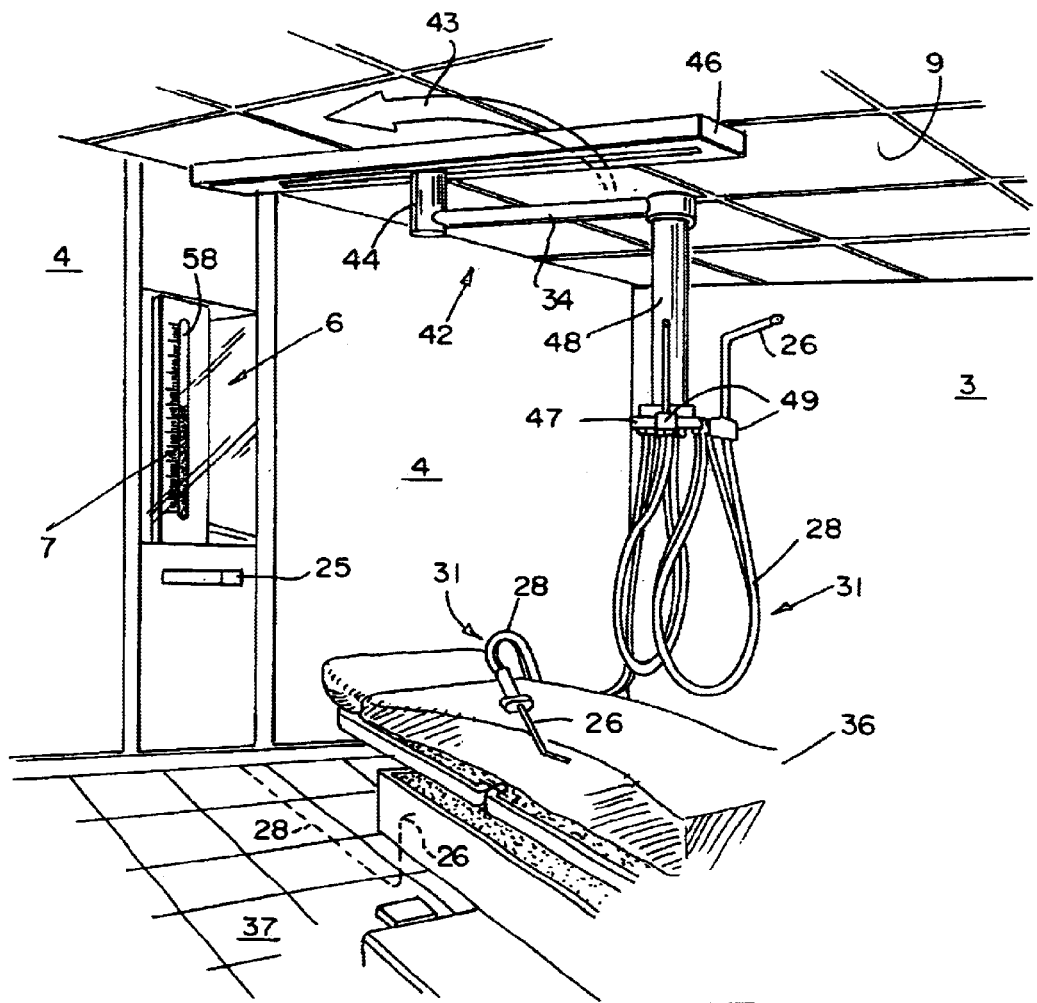
FIG. 1 is a perspective view of a portion of an operating room showing an articulated arm suspended from a ceiling of the operating room, a set of conduits of a fluid collection and disposal apparatus extending from a bottom of the articulated arm, each conduit terminating at a fluid collection handpiece, a transparent portion of a tank of the fluid collection and disposal apparatus being viewable through a window provided in a wall of the operating room, and the volume of fluid in the tank being viewable through the transparent portion of the tank.
Figure 2:
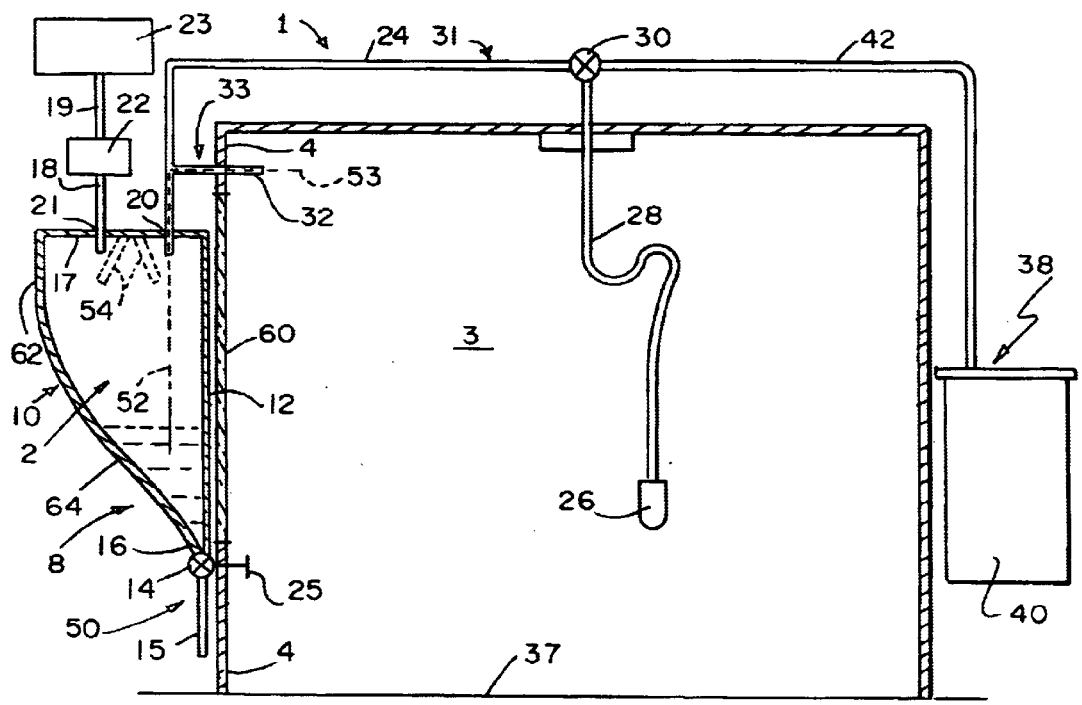
FIG. 2 is a diagrammatic view of portions of the fluid collection and disposal apparatus of FIG. 1 showing the tank on the left side of the page, a drainage system coupled to a bottom portion of the tank, a vacuum source coupled to an upper portion of the tank through a filter, a sampling system coupled to an upper portion of the tank and configured for obtaining fluid samples along a path indicated by a dotted line, and a cleaning system having a reservoir of a cleaning agent on the right side of the page.
Figure 3:
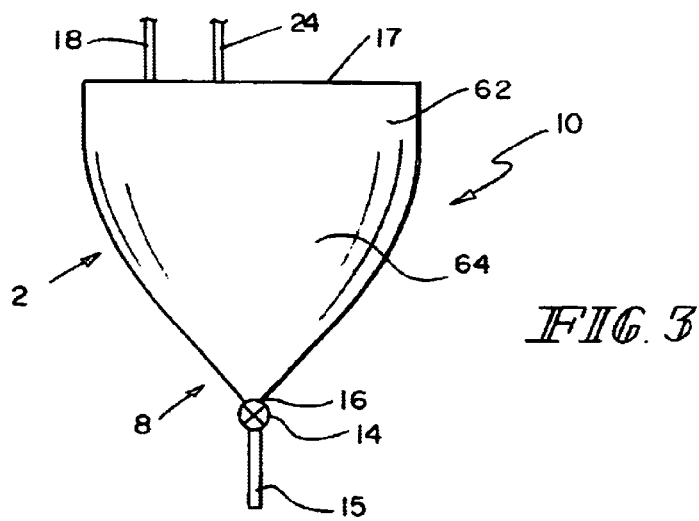
FIG. 3 is rear elevation view of the tank of the fluid collection and disposal apparatus of FIGS. 1 and 2 showing the tank having a narrow, lower portion and a broad, upper portion.

A fluid collection and disposal apparatus 1 according to this disclosure comprises a tank 2, shown in FIGS. 2 and 3, and one or more conduits 31 that are routed from tank 2 into an operating room 3 as shown in FIGS. 1 and 2. Blood and other fluids from a patient undergoing a medical procedure are suctioned through the conduits 31 into tank 2 for collection. Apparatus 1 is installed in a healthcare facility such that many of the larger components of apparatus 1 are situated outside operating room 3. In addition, the conduits extending from tank 2 are routed either above a ceiling 9 of operating room 3, below a floor 37 of operating room 3, through a wall 4 of operating room 3, or through various structures such as, for example, columns, pedestals, booms, and arms that are coupled to ceiling 9, floor 37, or walls 4 of operating room 3. By situating many of the components of apparatus 1 outside of operating room 3 and by at least partially concealing the conduits of apparatus 1, the amount of space taken up by apparatus 1 in operating room 3 is minimized.

In the illustrative embodiment of FIG. 1, conduits 31 comprise a set of hoses 28 that are routed upwardly through an articulated arm assembly 42 which is suspended from ceiling 9 of operating room 3. Illustrative arm assembly 42 includes a pivot joint 44 and an overhead arm 34 coupled to joint 44. Joint 44 is configured to permit arm 34 to pivot in a direction indicated by arrow 43 about a vertical axis. Arm assembly 42 further comprises a vertical arm 48 extending downwardly from an end of arm 34 that is distal from joint 44. A collar 47 is coupled to the lower end of vertical arm 48. Joint 44 is coupled to an elongated track member 46 of arm assembly 42 and is movable along the length of track member 46. Thus, caregivers are able to move arm assembly 42 into a desired position by pivoting arms 34, 48 about the vertical axis provided by joint 44 and by moving joint 44 and arms 34, 48 relative to track member 46.

Each of arms 34, 48, collar 47, joint 44, and track member 46 include interior regions or passages through which hoses 28 are routed. Hoses 48 are flexible to accommodate the various positions of arm assembly 42. In some embodiments, hoses 28 are disposable and are replaced between surgeries to help prevent fluid waste from one surgery from contaminating or intermixing with fluid waste of a subsequent surgery. Conduits 31 of illustrative apparatus 1 include a set of handpieces 26, each of which is coupled to an end of a respective hose 28. A plurality of brackets or clips 49 extend from collar 47. Handpieces 26 are coupled to clips 49 for storage and are decoupled from clips 49 for use during medical procedures.

Handpieces 26 are held by caregivers during medical procedures such that a tip of one or more handpieces 26 is placed at, in, or near the surgical site of the patient. Fluid waste from the patient is suctioned into hoses 28 through the tips of the handpieces 26 and through internal passageways of the handpieces 26. Thus, fluid waste enters apparatus 1 through handpieces 26. In some embodiments, handpieces 26 have triggers (not shown) that are actuated when suction is to be applied to the surgical site to vacuum fluid waste from the surgical site. It is within the scope of this disclosure for conduits 31 to include fluid suction heads or aspiration devices other than handpieces 26. For example, porous pads, nozzles, domes, perforated tubes, multi-channel suction heads, or any other type of device suitable for collecting fluid waste from a surgical site may be included as part of conduits 31 in lieu of handpieces 26.

Although illustrative apparatus 1 has hoses 28 routed upwardly through arm assembly 42, it is within the scope of this disclosure for hoses 28 to be routed downwardly through either a portion of operating table 36 or a pedestal (not shown) adjacent operating table 36 and then through floor 37 as indicated in FIG. 1 (in phantom). It is also within the scope of this disclosure for hoses 28 to connect to outlets (not shown) mounted on walls 4. In some embodiments, hoses 28 are routed through columns (not shown) that extend downwardly from ceiling 9 or that extend between floor 37 and ceiling 9. Furthermore, it is within the scope of this disclosure for arm assembly 42, pedestals, columns, or walls 4 through which conduits 31 are routed to have additional service outlets for delivering other types of medical services, such as oxygen, nitrous oxide, vacuum, waste anesthesia gas removal, etc. to operating room 3.

Conduit 31 of apparatus 1 has a three-way valve 30 to which one of hoses 28 couples as shown diagrammatically in FIG. 2. Conduit 31 further comprises a line 24 that extends from an outlet of valve 30 to tank 2. Although, valve 30 is shown above ceiling 9 of operating room 3 in FIG. 2, it is within the scope of this disclosure for valve 30 to be placed elsewhere. In embodiments having multiple hoses 28, such as the illustrative embodiment of FIG. 1, a manifold block (not shown) or a similar such device having a plurality of inlets, each of which couples to a respective hose 28, and a single outlet which couples to a first inlet port of valve 30 is provided. In some embodiments, conduit 31 includes a filter (not shown) positioned between valve 30 and tank 2 to capture fragments of tissue suctioned through handpiece 26 and hose 28.

In the illustrative embodiment of FIG. 2, handpiece 26, hose 28, valve 30, and line 24 cooperate to define conduit 31. The term "conduit," as used in this disclosure and in the claims, means any passageway or combination of passageways through which fluid is able to flow. Examples of conduits include, but are not limited to, any passageway or combination of passageways in one or more hoses, tubes, lines, pipes, manifolds, valves, service outlets, nozzles, filters, and the like, as well as combinations of these elements and the couplers that couple these elements together, and as well as passageways in devices held by caregivers and placed at, in, or near a surgical site on a patient.

Tank 2 of illustrative apparatus 1 is situated outside operating room 3 and receives fluid waste from conduit 31. In some embodiments, such as the embodiment shown in FIGS. 1 and 2, tank 2 is situated behind wall 4 of operating room 3. In this embodiment, tank 2 is either mounted directly to wall 4 or is supported by a frame, pedestal, stand, or other suitable support structure (not shown). In other embodiments, tank 2 is situated in a cabinet that is embedded in one of walls 4 of operating room 3 or is situated in a space behind a door that closes an opening formed in one of walls 4 of operating room 3. Thus, placing tank 2 in a supply or equipment closet adjacent to operating room 3 or in a corridor adjacent operating room 3 is within the scope of this disclosure. In still other embodiments, tank 2 is situated behind a movable wall panel that forms part of wall 4 of operating room 3. It is also within the scope of this disclosure for tank 2 to be located much further away from operating room 2 such as, for example, in a basement of a hospital or in a laboratory of the hospital that is remote from the operating room.

Illustrative tank 2 has a transparent portion 58 through which the contents of tank 2 are viewed. Illustrative wall 4 includes a wall panel 56 having a window or port 6 through which a caregiver can directly view the transparent portion 58 of tank 2 to see the contents therein. In some embodiments, wall panel 56 includes a transparent window pane 60 in window 6 as shown in FIG. 2. In other embodiments, window 6 is open and tank 2 is configured so that a small portion of tank 2 extends into operating room 3 through window 6 as shown in FIG. 1. Therefore, when it is stated in this disclosure and in the claims that the tank is "outside the operating room," it is meant that all or almost all of the tank is outside the volume of space defined by the surfaces of walls 4, ceiling 9, and floor 37 that bound the associated operating room. Thus, a tank having a small portion (i.e. a minority portion of the tank), such as transparent portion 58, that projects slightly beyond wall or that is otherwise located in the space bounded by the walls, ceiling, and floor of an operating room, is also considered to be "outside the operating room" according to this disclosure.

Transparent portion 58 enables the fill level of fluid waste in tank 2 to be seen directly. However, it is within the scope of this disclosure for apparatus 1 to have a float in the interior region of tank 2 that rises with and falls with the level of fluid waste in tank 2 and that is coupled mechanically or electrically to an indicator, such as a gage or a digital display, that provides a readout corresponding to the level of fluid waste in tank 2.

A plurality of graduated markings 7 are formed in, or are otherwise provided on, the portion of illustrative tank 2 adjacent transparent portion 58 as shown in FIG. 1. Tank 2 has a narrow, lower portion 8 and a broad, upper portion as shown in FIGS. 2 and 3. Therefore, the spacing between markings 7 associated with lower portion 8 indicate a smaller incremental amount of fluid waste than similarly spaced markings 7 associated with upper portion 10. That is, the markings 7 associated with lower portion 8 permit a more accurate volume measurement than the markings 7 associated with upper portion 10. The increased accuracy of the markings 7 associated with lower portion 8 of tank 2 are useful when a relatively small amount of fluid waste is suctioned into tank 2, such as during a surgical procedure on a child. In one embodiment, markings 7 are configured to provide measurement accuracy for volumes between 0 and 25 ml of +/−1 ml; for volumes between 25 and 250 ml, +/−5 ml; and for volumes greater than 250 ml, +/−50 ml.

Illustrative tank 2 has a flat, vertical wall 12 that is positioned in or adjacent to window 6. Transparent portion 58 is included as part of wall 12 or is coupled to wall 12. Illustrative tank 2 also has a semi-cylindrical wall 62 and a semi-frustoconical wall 64, each of which is appended to vertical wall 12. Wall 62 transitions smoothly into wall 64 as shown in FIGS. 2 and 3. Wall 62 is associated with broad, upper portion 10 of tank 2 and wall 64 is associated with the narrow, lower portion 8 of tank 2. In alternative embodiments, tank 2 has other shapes. For example, tank 2 may have a lower, small semi-cylindrical portion; an upper, large semi-cylindrical portion; and a semi-frustoconical portion interconnecting the small and large semi-cylindrical portions. It is also within the scope of this disclosure for tank 2 to have cylindrical and frustoconical portions in lieu of flat wall 12 and semi-cylindrical and semi-frustoconical portions, respectively. In still further embodiments, tank 2 has a large, box-like upper portion; a small, box-like lower portion; and a transition portion having inclined panels between the box-like upper and lower portions.

In the embodiment shown diagrammatically in FIG. 2, tank 2 is spaced apart from wall 4 to provide room for a lighting source that illuminates flat wall 12 and transparent portion 58 to enhance the visibility of the level of fluid in tank 2. However, it is within the scope of this disclosure for other types of lighting systems (not shown), including light sources inside tank 2, light sources mounted on walls 4 or ceiling 9 that are specifically directed at transparent portion 58 through window 6, or regular room lights in operating room 3 that are not specifically directed at transparent portion 58 but that provide light through window 6 onto transparent portion 58, to be used to illuminate the contents of tank 2.

Tank 2 has an opening (not shown) at a bottom end 16 of lower portion 8. A valve 14 is coupled to bottom end 16 of tank 2 so that an inlet of valve 14 is in communication with the interior region of tank 2 through the opening formed in bottom end 16. An outlet of valve 14 is coupled to a pipe or line 15 which routes either to larger, hazardous waste collection tank (not shown) that is located remotely in the healthcare facility. Valve 14 and line 15, as well as the hazardous waste collection tank, define a drainage system 50 of apparatus 1. Valve 14 is movable, either manually or via an electrically controlled actuator, between an opened position in which the fluid waste in tank 2 is flushed or drained from tank 2 into line 15 and a closed position in which the fluid waste is prevented from being flushed or drained from tank 2 into line 15.

Drainage system 50 includes a user input 25 that is operated to move valve 14 from the closed position to the opened position. In the illustrative embodiment of FIGS. 1 and 2, a portion of user input 25 is accessible to caregivers in operating room 3. In those embodiments where valve 14 is manually operated, user input 25 comprises either a lever or a knob that is moved manually by the caregiver. In those embodiments where valve 14 is operated automatically, the user input comprises a button that is pressed by a caregiver to signal a control system of apparatus 1 that fluid waste in tank 2 is to be flushed or drained. The control system then provides signals to the electrically controlled actuator to move valve 14 to the opened position. The control system, in some embodiments, is configured so that a single, momentary press of the button by the caregiver moves valve 14 from the closed position to the opened position for a predetermined period of time and then moves valve 14 back to the closed position.

Illustrative tank 2 includes a top 17 having two ports 20, 21 as shown in FIG. 2. Top 17 is removable so that maintenance personnel can gain access to the interior region of tank 2, if necessary. Line 24 communicates with the interior region of tank 2 through port 20. A suction source 23 communicates with the interior region of tank 2 through port 21. In the illustrative embodiment, a filter 22 is situated between port 21 and suction source 23. A first line 19 extends between suction source 23 and filter 22. A second line 18 extends between filter 22 and port 21. Thus, suction source 23 communicates with the interior region of tank 2 through lines 18, 19, port 21, and filter 22. In some embodiments, suction source 23 is the hospital's "house vacuum." In such embodiments, line 19 includes a connector that couples to a service outlet associated with the house vacuum. In other embodiments, suction source 23 is a pump or compressor that is located in close proximity to tank 2. For example, mounting a pump or compressor to any of wall 4, tank 2, or any structure supporting tank 2 is within the scope of this disclosure.

Suction source 23 operates to create a negative pressure in tank 2. When valve 30 is moved to a position having line 24 in communication with one or more of hoses 28, the negative pressure established in tank 2 by suction source 23 is communicated to the associated handpieces 26 through line 24, valve 30, and hose 28. In some embodiments, apparatus 1 includes a pressure sensor in tank 2 and a control valve associated with either line 18, line 19, or port 21. In such an embodiment, apparatus 1 includes an actuator that operates to open or close the control valve, depending upon the pressure sensed by the pressure sensor. Thus, the pressure sensor, the control valve, and the actuator, along with any associated circuitry, provide apparatus 1 with a feedback control system that operates to control the amount of negative pressure established in tank 2 by suction source 23.

Filter 22 prevents fluid waste or waste vapor having biological particulates from reaching vacuum source 23. In some embodiments, filter 22 includes a hydrophobic filter element. However, any type of filter element configured to prevent fluid waste or waste vapor from reaching suction source 23 is within the scope of this disclosure. It is also within the scope of this disclosure for filter 22 to include charcoal for absorbing odors associated with the fluid waste contained in tank 2. Furthermore, it is within the scope of this disclosure for filter 22 to be accessible to caregivers or maintenance personnel for removal, replacement, or cleaning.

In the illustrative embodiment, apparatus 1 includes a sampling system 33 that permits samples of fluid waste to be taken from tank 2. In some embodiments, sampling system 33 comprises a sampling tube 32 that extends from line 24 of conduit 31 into room 3. A sample of fluid waste flowing through line 24 may be obtained along a path 53, shown in FIG. 2 (in phantom), by a caregiver in operating room 3 during a medical procedure. For example, the caregiver may insert one end of a collection conduit through tube 32 and into line 24 to divert at least a portion of the fluid waste from line 24 through the collection conduit and into a fluid sampling receptacle in which the other end of the collection conduit is received, or else, the caregiver may attach a suction device to tube 32 and withdraw a portion of the fluid waste flowing in line 24 into a fluid sampling receptacle associated with the suction device.

In another embodiment, sampling system 33 includes a sampling valve (not shown) at the junction of tube 32 and line 24 that is movable, either manually or via an electrically controlled actuator, between a first position in which fluid waste flows through line 24 into tank 2 and a second position in which fluid is diverted into tube 32 for collection. In such an embodiment, a user input is situated in operating room 3 and is operated by the caregiver to move the sampling valve between the first and second positions. In the case of a manually operated sampling valve, the user input comprises either a lever or a knob that is moved manually by the caregiver. In the case of an automatically controlled valve, the user input comprises a button that is pressed by a caregiver to signal a control system of apparatus 1 that a sample is to be taken. The control system then provides signals to the electrically controlled actuator to move the sampling valve. The control system, in some embodiments, is configured so that a single, momentary press of the button by the caregiver moves the sampling valve from the first position to the second position for a predetermined period of time and then moves the sampling valve back to the first position.

In a further embodiment, sampling system 33 comprises a telescopic arm that extends and retracts along a path 52 shown in FIG. 2 (in phantom). In the extended position, a bottom segment of the telescopic arm is submerged, at least partially, in the fluid waste. A caregiver then uses a suction device, such as a squeeze bulb or house suction, to apply suction to tube 32 which is in fluid communication with the telescopic arm. The suction applied by the caregiver to tube 32 causes fluid waste to flow upwardly through the telescopic arm, through tube 32, and then into a sample collection receptacle associated with the suction device.

The fluid waste may be stratified as a result of being deposited in tank 2 in layers which may have different characteristics. Therefore, in some embodiments, apparatus 1 includes a control system that enables the caregiver to control the depth that the telescopic arm descends into the fluid waste contained in tank 2 so that a sample is obtained from a desired layer. In such embodiments, the telescopic arm is positioned in tank 2 close to transparent portion 58 so that the caregiver is able to see the position of the bottom segment of the telescopic arm. The control system that extends and retracts the telescopic arm is operated manually in some embodiments and automatically in other embodiments.

In the embodiment of FIG. 2, the telescopic arm which moves along path 52 and tube 32 which defines path 53 are both shown to be in communication with line 24. However, it is within the scope of this disclosure for sampling system 33 not to be in communication with line 24. In such embodiments, top 17 of tank has an additional port (not shown) which receives associated components of sampling system 33.

Apparatus 1 includes a cleaning system 38 as shown diagrammatically in FIG. 2. Cleaning system 38 includes a reservoir 40 that contains disinfectant and water. The disinfectant and water may be premixed in reservoir 40 prior to usage or may be separated from one another until just before usage when they are mixed together. The disinfectant and water cooperate to define a cleaning agent. System 38 further includes a line 45 that extends from reservoir 40 to valve 30. After a surgical procedure, valve 30 is moved to a position having line 24 in communication with line 42. In some embodiments, cleaning system 38 includes a pump (not shown), that is located in the interior region of reservoir 40, for example, and that operates to move the cleaning agent from reservoir 40 through lines 24, 42, and valve 30 into tank 2.

In some embodiments, a cleaning cycle of cleaning system 38 is initiated automatically when user input 25 is operated to actuate valve 14 to drain or flush the fluid waste from tank 2. In such embodiments, a control system receives an input from a position sensor, for example, which indicates that user input 25 has been engaged to evacuate the fluid waste from tank 2. The control system then sends a signal to an actuator that moves valve 30 to the position having line 42 in communication with line 24 and the control system signals the pump of cleaning system 38 to start pumping the cleaning agent from reservoir 40 to tank 2.

When the cleaning cycle is initiated automatically by actuation of valve 14, the cleaning agent, in some embodiments, or water without the disinfectant, in other embodiments, enters tank 2 before all of the fluid waste has exited tank 2 through valve 14. It is under these conditions that the tank 2 is considered to be "flushed." In other embodiments, where the cleaning cycle is not initiated automatically by actuation of valve 14, the cleaning cycle of cleaning system 38 is initiated by pressing a button on a control panel (not shown) after the fluid waste has been completely drained from tank 2. During the cleaning cycle, valve 14 is initially opened so that the cleaning agent entering tank 2 is flushed out of tank 2 along with the fluid waste and then valve 14 closes so that the cleaning agent accumulates in tank 2. In some embodiments, valve 14 is opened and closed several times during the cleaning cycle.

During the cleaning cycle, a valve (not shown) associated with either port 21 or line 18 is closed and the cleaning agent is introduced into tank 2 through one or more nozzles or jets 54. Jets 54 are in fluid communication with line 24 through a cleaning valve (not shown) and a short conduit (not shown). The cleaning valve is situated just above port 20 and operates during the cleaning cycle to divert the cleaning agent away from the portion of line 24 received in port 20 and into the short conduit that leads to jets 54. The cleaning agent exits jets 54 as a pressurized spray that impinges upon the interior surfaces of walls 12, 62, 64 and top 17 of tank 2 to physically remove any fluid waste residue that remains adhered thereto during flushing of tank 2 or after tank 2 is drained. In addition, the cleaning agent chemically disinfects tank 2.

After the cleaning agent is sprayed into tank 2 through jets 54 for a predetermined period of time, cleaning system 38 enters a rinse cycle during which water without disinfectant is sprayed into tank 2 through jets 54 for a predetermined period of time, which may be less or more than the time associated with the cleaning cycle. During the rinse cycle, valve 14 opens and drains the contents of tank 2. After one or more rinse cycles, valve 14 closes in preparation for the next use. In some embodiments, jets 54 are permanently mounted to top 17 of tank 2, and in other embodiments, jets 54 are lowered into tank 2 through an associated port or ports in top 17 of tank 2 upon the initiation of the cleaning cycle. Cleaning system 38 operates so that the entire cleaning, disinfecting, and rinsing cycle takes a relatively short period of time, approximately five minutes, for example, so that the wait time between cleaning and availability for use in a subsequent surgical procedure is minimized.

As mentioned above, hoses 28 are replaced between surgeries in some embodiments. In other embodiments, cleaning system 38 is operated to clean hoses 28. In such embodiments, handpieces 26 are decoupled from the ends of hoses 28. Thereafter, the free end of the hose 28 to be cleaned is attached to tube 32 and a button is engaged on a control panel (not shown) in operating room 3 to signal control circuitry of apparatus 1 to clean the hose. In those embodiments having multiple hoses 28, the hoses 28 are numbered and the control panel includes separate buttons that indicate which of the numbered hoses 28 are to be cleaned. Valve 30 is moved to a position so that line 42 is no longer in communication with line 24 through valve 30, but rather so that line 42 is in communication with the hose 28 to be cleaned. Thereafter, the pump of cleaning system 38 is operated to pump the cleaning agent from reservoir 40 to tank 2 through each of the following: line 42, valve 30, the hose 28 selected by the caregiver, tube 32, and the segment of line 24 between tube 32 and tank 2. After the hose 28 coupled to tube 32 is cleaned, cleaning system 38 enters a rinse cycle during which water without disinfectant is pumped through these same elements. Each of the other hoses 28 are cleaned and rinsed in a similar manner.

In some embodiments, handpieces 26 are disposed of between patient uses and replaced with new handpieces 26. In other embodiments, handpieces 26 are placed in an autoclave apparatus for cleaning and sterilization. In still other embodiments, handpieces 26 are immersed in a solution of disinfectant followed by a water rinse. Hoses 28 may also be immersed in a solution of disinfectant and then rinsed with water rather than being discarded.

Emulsified fats may tend to collect in tank 2 and conduits 31. To eliminate buildup of emulsified fats in tank 2 and conduits 31, an enzyme may be added to the disinfectant and water solution (as part of the cleaning agent) in reservoir 40.

Apparatus 1 includes one or more indicators or alarms (not shown) that provide either a visual or audible indication of various alarm conditions occurring in the various systems of apparatus 1. For example, one alarm condition occurs when the amount of fluid in tank 2 exceeds a maximum amount. Another example of an alarm condition is the absence of suction in tank 2. Such alarm conditions are communicated to the caregivers in operating room 3 by visual messages or images appearing on a display screen of the control panel of apparatus 1, by activation of a speaker or buzzer housed in the control panel, or both.

Other sensors are included in some embodiments of apparatus 1 for sensing various normal operating conditions of apparatus 1. Some such sensors are described above. Another example of a sensor included in some embodiments of apparatus 1, is a sensor that senses fluid drainage into the tank 2. If the fluid drainage sensor senses the absence of fluid drainage for longer than some predetermined period of time, such as ten minutes, for example, a message appears on the display screen of the control panel querying whether the medical procedure is complete and querying whether tank 2 should be drained or flushed.

Although certain illustrative embodiments have been described in detail above, variations and modifications exist within the scope and spirit of this disclosure as described and as defined in the following claims.

What is claimed is:

1. An apparatus for collecting and disposing of fluid waste from a patient undergoing a medical procedure in an operating room having a floor, a ceiling, and walls, the apparatus comprising a tank located outside the operating room, and a conduit extending from a location inside the operating room to the tank positioned outside the operating room, the fluid waste from the patient being suctioned through the conduit and into the tank for collection, and a sampling system that is operable to obtain a sample of the fluid waste contained in the tank, a first portion of the sampling system being positioned in the tank and a second portion of the sampling system being positioned in the operating room.

2. The apparatus of claim 1, further comprising a vacuum source coupled to the tank to suction the fluid waste through the conduit into the tank.

3. The apparatus of claim 1, wherein the tank includes an upper, broad portion and a lower, narrow portion, and the conduit is coupled to the upper, broad portion.

4. The apparatus of claim 3, further comprising a drainage system coupled to the lower, narrow portion to drain fluid waste from the tank.

5. The apparatus of claim 1, further comprising an indicator that indicates a quantity of fluid waste contained in the tank.

6. The apparatus of claim 1, further comprising an overhead arm and the conduit being coupled to the overhead arm.

7. The apparatus of claim 1, wherein the conduit is routed to the tank through the floor.

8. The apparatus of claim 1, wherein the tank includes a transparent portion for observing fluid waste contained in the tank.

9. The apparatus of claim 8, wherein the transparent portion is adapted to be received in a port formed in one of the walls of the operating room.

10. AC The apparatus of claim 1, wherein the tank has a port and the first portion of the sampling system includes a telescopic arm that extends through the port into the tank to obtain the sample.

11. The apparatus of claim 1, further comprising a cleaning system coupled to the tank and to the conduit, the cleaning system being operable to clean the tank and the conduit, and the cleaning system being positioned outside the operating room.

12. The apparatus of claim 11, wherein the conduit includes a valve, the cleaning system includes a reservoir configured to receive a cleaning agent, and the cleaning system includes a delivery conduit coupled to the reservoir and to the valve.

13. The apparatus of claim 11, wherein the cleaning system includes a jet coupled to the tank and the jet being configured to deliver a cleaning agent into the tank to clean the tank.

14. An apparatus for collecting and disposing of fluid waste from a patient undergoing a medical procedure in an operating room, the apparatus comprising a tank, and a conduit coupled to the tank to conduct fluid waste to the tank for collection in the tank, the tank including a narrow portion and a broad portion to allow more accurate measurement of fluid waste in the narrow portion than in the broad portion, and a drainage system coupled to the narrow portion to drain fluid waste from the tank.

15. The apparatus of claim 14, further comprising an indicator that indicates a volume of fluid waste contained in the tank, the indicator having graduated markings for measuring the volume of the fluid waste, the spacing of the graduated marking being such that fluid waste measurements associated with small volumes of fluid waste having maximum fluid levels in the narrow portion of the tank are more accurate than fluid measurements associated with large volumes of fluid waste having maximum fluid levels in the broad portion of the tank.

16. The apparatus of claim 14, wherein the broad portion is positioned to lie above the narrow portion.

17. The apparatus of claim 14, wherein the conduit is coupled to the broad portion.

18. The apparatus of claim 14, further comprising a vacuum source coupled to the broad portion to suction fluid waste through the conduit and into the tank.

19. The apparatus of claim 14, wherein the drainage system includes a valve coupled to the narrow portion to control drainage of fluid waste from the tank.

20. The apparatus of claim 14, wherein the tank is positioned outside the operating room, and the conduit extends from a location inside the operating room to the tank positioned outside the operating room.

21. A method for collecting and disposing of fluid waste from a patient undergoing a medical procedure in an operating room, the method comprising the steps of creating a negative pressure in a tank positioned outside the operating room, and suctioning fluid waste from the patient through a conduit that is routed from the tank into the operating room, and observing the tank through a port of a wall of the operating room.

22. The method of claim 21, wherein the suctioning step comprises suctioning fluid waste from the patient through a conduit that is routed from the tank, through a space above a ceiling of the operating room, and downwardly from the ceiling into the operating room.

23. The method of claim 22, wherein the suctioning step comprises suctioning fluid waste from the patient through a conduit that is routed from the tank, through a floor of the operating room, and upwardly from the floor into the operating room.

24. The method of claim 21, wherein the observing step includes the step of observing an interior region of the tank through a transparent portion of the tank.

25. The method of claim 21, further comprising the step of ascertaining a quantity of fluid waste collected in the tank.

26. The method of claim 25, wherein the ascertaining step comprises looking at a plurality of graduated markings having a higher resolution of measurement at a lower, narrow portion of the tank than at an upper, broad portion of the tank.

27. The method of claim 21, further comprising the step of draining fluid waste from the tank.

28. The method of claim 27, wherein the draining step includes the step of actuating a valve.

29. The method of claim 21, further comprising the step of cleaning the tank.

30. The method of claim 29, wherein the cleaning step includes the step of directing a cleaning agent from a reservoir containing the cleaning agent into the tank.

31. The method of claim 30, wherein the cleaning step includes the step of actuating a valve that is situated in a conduit which extends between the reservoir and the tank.

32. The method of claim 30, wherein the cleaning step includes the step of suctioning the cleaning agent from the reservoir to the tank.

33. The method of claim 29 wherein the cleaning step includes the step of spraying a cleaning agent from a jet positioned inside the tank.

34. The method of claim 21, further comprising the step of draining the fluid waste from the tank, the tank being maintained stationary during the suctioning step and during the draining step.

35. The method of claim 34, further comprising the steps of cleaning the tank after the draining the step, the tank being maintained stationary during the suctioning, draining, and cleaning steps.

36. A method for collecting and disposing of fluid waste from a patient undergoing a medical procedure in an operating room, the method comprising the steps of creating a negative pressure in a tank positioned outside the operating room, and suctioning fluid waste from the patient through a conduit that is routed from the tank into the operating room, and through one of a floor of the operating room or a ceiling of the operating room, and through an arm pivotable about an axis located in the operating room, and obtaining a sample of fluid waste from of the tank and the conduit.

37. The method of claim 36, wherein the obtaining step comprises the step of extending a telescopic arm through a port into the tank to obtain the sample.

38. An apparatus for collecting and disposing of fluid waste from a patient undergoing a medical procedure in an operating room having walls, the apparatus comprising a tank located outside the operating room, the tank having a transparent portion, a conduit extending from a location inside the operating room to the tank positioned outside the operating room, a vacuum source coupled to the tank to suction the fluid waste through the conduit into the tank, and a port formed in one of the walls of the operating room for observing fluid waste contained in the tank from inside the operating room through the transparent portion of the tank.

* * * * *